United States Patent [19]
Schwan

[11] 3,966,759
[45] June 29, 1976

[54] 1-(3,4-DICHLOROBENZYL)-3-INDAZOLINONE

[75] Inventor: Thomas J. Schwan, Norwich, N.Y.

[73] Assignee: Morton-Norwich Products, Inc., Norwich, N.Y.

[22] Filed: Mar. 7, 1975

[21] Appl. No.: 556,479

[52] U.S. Cl. .................. 260/310 A; 260/310 C; 424/273
[51] Int. Cl.² .............. C07D 231/56; A61K 31/415
[58] Field of Search .................. 260/310 C, 310 A

[56] References Cited
FOREIGN PATENTS OR APPLICATIONS
1,214,109  12/1970  United Kingdom Primary Examiner—Donald B. Moyer
Attorney, Agent, or Firm—Anthony J. Franze

[57] ABSTRACT
The title compound is useful as an anthelmintic.

1 Claim, No Drawings

1-(3,4-DICHLOROBENZYL)-3-INDAZOLINONE

This invention is concerned with the compound 1-(3,4-dichlorobenzyl)-3-indazolinone. This compound possesses anthelmintic properties. When administered perorally to mice harboring *Ascaris suum* in a dose of 100 mg/kg b.i.d. for five days, a 79% reduction in worm population is secured.

In order that this invention may be available to and understood by those skilled in the art, the following method for its preparation is set forth:

1-(3,4-Dichlorobenzyl)-3-indazolinone

A mixture of 13.4 g (0.10 mole) of 3-indazolinone, 21.45 g (0.11 mole) 3,4-dichlorobenzyl chloride, 15.0 g (0.10 mole) NaI, and 13.8 g (0.10 mole) $K_2CO_3$ in 175 ml DMF was stirred and refluxed for 15 hours and then concentrated to dryness in vacuo. The residue was partitioned between 300 ml $CHCl_3$ and 200 ml $H_2O$. The $CHCl_3$ layer was separated and the aqueous layer was extracted with an additional 200 ml $CHCl_3$. The combined organic extracts were concentrated to dryness and the residue was recrystallized from 450 ml $CH_3CN$ to give 11.7 g (40%) of the product, m.p. 175°–187°. The analytical sample, m.p. 185°–187°, was obtained by recrystallization from absolute ethanol.

Anal. Calcd. for $C_{14}H_{10}Cl_2N_2O$: C, 57.36; H, 3.44; N, 9.56. Found: C, 57.25; H, 3.57; N, 9.34.

What is claimed is:

1. 1-(3,4-Dichlorobenzyl)-3-indazolinone

\* \* \* \* \*